United States Patent
Foshee

(10) Patent No.: US 12,426,889 B2
(45) Date of Patent: *Sep. 30, 2025

(54) SURGICAL CLIP

(71) Applicant: TELEFLEX MEDICAL INCORPORATED, Morrisville, NC (US)

(72) Inventor: David Lee Foshee, Apex, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/680,836

(22) Filed: May 31, 2024

(65) Prior Publication Data

US 2024/0315705 A1 Sep. 26, 2024

Related U.S. Application Data

(63) Continuation of application No. 18/196,979, filed on May 12, 2023, now Pat. No. 11,998,215, which is a
(Continued)

(51) Int. Cl.
*A61B 17/122* (2006.01)
*A61B 17/00* (2006.01)
*A61B 17/12* (2006.01)

(52) U.S. Cl.
CPC .. *A61B 17/122* (2013.01); *A61B 2017/00004* (2013.01); *A61B 2017/00862* (2013.01); *A61B 2017/12004* (2013.01)

(58) Field of Classification Search
CPC ....... A61B 17/08; A61B 17/083; A61B 17/12; A61B 17/122; A61B 17/1227;
(Continued)

(56) References Cited

U.S. PATENT DOCUMENTS

| | | | |
|---|---|---|---|
| 1,728,322 A | 9/1929 | Badrian |
| 2,384,697 A | 9/1945 | Riccardi |

(Continued)

FOREIGN PATENT DOCUMENTS

| | | | |
|---|---|---|---|
| CN | 101507646 A | 8/2009 |
| CN | 101543418 A | 9/2009 |

(Continued)

OTHER PUBLICATIONS

Beveled Definition & Meaning—Merriam-Webster (Year: 2023).
(Continued)

*Primary Examiner* — Ryan J. Severson
(74) *Attorney, Agent, or Firm* — BakerHostetler

(57) ABSTRACT

A surgical clip may include first and second leg members, each having inner surfaces. The inner surface of the first leg member may be concave and the inner surface of the second leg member may be convex. The surgical clip may include a first locking member positioned on a distal end portion of the first leg member, and a second locking member positioned on a distal end portion of the second leg member. The surgical clip may also include a third locking member position between a proximal end portion and the distal end portion of the first leg member, and a fourth locking member positioned between a proximal end portion and the distal end portion of the second leg member. The first and second locking members, and the third and fourth locking members may be configured to interact to secure the surgical clip in a closed configuration.

17 Claims, 9 Drawing Sheets

Related U.S. Application Data continuation of application No. 16/762,442, filed as application No. PCT/US2018/060946 on Nov. 14, 2018, now Pat. No. 11,648,014.

(60) Provisional application No. 62/585,795, filed on Nov. 14, 2017.

(58) Field of Classification Search
CPC .......... A61B 2017/00004; A61B 2017/00862; A61B 2017/12004; A61F 6/206
See application file for complete search history.

(56) References Cited

U.S. PATENT DOCUMENTS

| | | |
|---|---|---|
| 2,498,372 A | 2/1950 | Kortlucke et al. |
| 2,598,901 A | 6/1952 | Garland |
| 2,626,608 A | 1/1953 | Garland |
| 2,635,238 A | 4/1953 | Garland |
| 3,171,184 A | 3/1965 | Lage |
| 3,503,397 A | 3/1970 | Fogarty et al. |
| 3,766,925 A | 10/1973 | Rubricius |
| 3,825,012 A | 7/1974 | Nicoll |
| 3,867,944 A | 2/1975 | Samuels |
| 3,874,042 A | 4/1975 | Eddleman et al. |
| 3,924,629 A | 12/1975 | Akiyama |
| 4,212,303 A | 7/1980 | Nolan |
| 4,227,730 A | 10/1980 | Alexander et al. |
| 4,337,774 A | 7/1982 | Perlin |
| 4,340,061 A | 7/1982 | Kees et al. |
| 4,345,600 A | 8/1982 | Rothfuss |
| 4,346,869 A | 8/1982 | MacNeill |
| 4,390,019 A | 6/1983 | Leveen et al. |
| 4,418,694 A | 12/1983 | Beroff et al. |
| 4,434,795 A | 3/1984 | Mericle |
| 4,449,531 A | 5/1984 | Cerwin et al. |
| 4,450,840 A | 5/1984 | Mericle et al. |
| 4,458,682 A | 7/1984 | Cerwin |
| 4,476,865 A | 10/1984 | Failla et al. |
| 4,487,205 A | 12/1984 | Di et al. |
| 4,519,392 A | 5/1985 | Lingua |
| 4,527,562 A | 7/1985 | Mericle |
| 4,550,729 A | 11/1985 | Cerwin et al. |
| 4,558,699 A | 12/1985 | Bashour |
| 4,579,118 A | 4/1986 | Failla |
| 4,588,160 A | 5/1986 | Flynn et al. |
| 4,589,626 A | 5/1986 | Kurtz et al. |
| 4,638,804 A | 1/1987 | Jewusiak |
| 4,667,671 A | 5/1987 | Danzig |
| 4,673,161 A | 6/1987 | Flynn et al. |
| 4,712,549 A | 12/1987 | Peters et al. |
| 4,716,886 A | 1/1988 | Schulman et al. |
| 4,726,372 A | 2/1988 | Perlin |
| 4,807,622 A | 2/1989 | Ohkaka et al. |
| 4,822,348 A | 4/1989 | Casey |
| 4,834,096 A | 5/1989 | Oh et al. |
| 4,844,066 A | 7/1989 | Stein |
| 4,870,965 A | 10/1989 | Jahanger |
| 4,936,447 A | 6/1990 | Peiffer |
| 4,938,215 A | 7/1990 | Schulman et al. |
| 4,938,765 A | 7/1990 | Rasmusson |
| 4,942,886 A | 7/1990 | Timmons |
| 4,950,275 A | 8/1990 | Donini |
| 4,955,897 A | 9/1990 | Ship |
| 4,961,499 A | 10/1990 | Kulp |
| 4,972,949 A | 11/1990 | Peiffer |
| 4,976,722 A | 12/1990 | Failla |
| 5,002,552 A | 3/1991 | Casey |
| 5,009,657 A | 4/1991 | Cotey et al. |
| 5,026,382 A | 6/1991 | Peiffer |
| 5,046,611 A | 9/1991 | Oh |
| 5,047,038 A | 9/1991 | Peters et al. |
| 5,062,846 A | 11/1991 | Oh et al. |
| 5,078,731 A | 1/1992 | Hayhurst |
| 5,100,416 A | 3/1992 | Oh et al. |
| 5,104,395 A | 4/1992 | Thornton et al. |
| 5,112,343 A | 5/1992 | Thornton |
| 5,127,915 A | 7/1992 | Mattson |
| 5,160,339 A | 11/1992 | Chen et al. |
| 5,171,251 A | 12/1992 | Bregen et al. |
| 5,171,252 A | 12/1992 | Friedland |
| 5,171,253 A | 12/1992 | Klieman |
| 5,201,416 A | 4/1993 | Taylor |
| 5,222,961 A | 6/1993 | Nakao et al. |
| 5,234,449 A | 8/1993 | Bruker et al. |
| 5,242,456 A | 9/1993 | Nash et al. |
| 5,259,405 A | 11/1993 | Hua-Chou |
| 5,279,416 A | 1/1994 | Malec et al. |
| 5,330,442 A | 7/1994 | Green et al. |
| 5,330,487 A | 7/1994 | Thornton et al. |
| 5,366,458 A | 11/1994 | Korthoff et al. |
| 5,366,459 A | 11/1994 | Yoon |
| 5,376,101 A | 12/1994 | Green et al. |
| 5,395,381 A | 3/1995 | Green et al. |
| 5,409,499 A | 4/1995 | Yi |
| 5,441,509 A | 8/1995 | Vidal et al. |
| 5,462,555 A | 10/1995 | Bolanos et al. |
| 5,474,572 A | 12/1995 | Hayhurst |
| 5,474,732 A | 12/1995 | Korthoff et al. |
| 5,487,746 A | 1/1996 | Yu et al. |
| 5,501,693 A | 3/1996 | Gravener |
| 5,509,920 A | 4/1996 | Phillips et al. |
| 5,549,621 A | 8/1996 | Bessler et al. |
| 5,575,802 A | 11/1996 | McQuilkin et al. |
| 5,626,592 A | 5/1997 | Phillips et al. |
| 5,667,516 A | 9/1997 | Allen |
| 5,676,676 A | 10/1997 | Porter |
| 5,697,938 A | 12/1997 | Jensen et al. |
| 5,713,911 A | 2/1998 | Racenet et al. |
| 5,713,912 A | 2/1998 | Porter |
| 5,722,982 A | 3/1998 | Ferreira et al. |
| 5,725,542 A | 3/1998 | Yoon |
| 5,810,853 A | 9/1998 | Yoon |
| 5,846,255 A | 12/1998 | Casey |
| 5,908,430 A | 6/1999 | Appleby |
| 5,921,991 A | 7/1999 | Whitehead et al. |
| 5,925,052 A | 7/1999 | Simmons |
| 5,947,980 A | 9/1999 | Jensen et al. |
| 5,997,548 A | 12/1999 | Jahanger |
| 6,015,417 A | 1/2000 | Reynolds, Jr. |
| RE36,720 E | 5/2000 | Green et al. |
| 6,099,539 A | 8/2000 | Howell et al. |
| 6,131,576 A | 10/2000 | Davis |
| 6,206,896 B1 | 3/2001 | Howell et al. |
| 6,210,419 B1 | 4/2001 | Mayenberger et al. |
| 6,217,590 B1 | 4/2001 | Levinson |
| 6,261,303 B1 | 7/2001 | Mayenberger et al. |
| 6,273,903 B1 | 8/2001 | Wilk |
| 6,305,387 B1 | 10/2001 | Atchison |
| 6,312,445 B1 | 11/2001 | Fogarty et al. |
| 6,348,057 B1 | 2/2002 | Porat |
| 6,349,727 B1 | 2/2002 | Stewart, Jr. |
| 6,387,106 B1 | 5/2002 | Howell et al. |
| 6,391,035 B1 | 5/2002 | Appleby et al. |
| 6,419,682 B1 | 7/2002 | Appleby et al. |
| 6,461,368 B2 | 10/2002 | Fogarty et al. |
| 6,485,503 B2 | 11/2002 | Jacobs et al. |
| 6,537,289 B1 | 3/2003 | Kayan et al. |
| 6,638,282 B2 | 10/2003 | Ramsey et al. |
| 6,699,258 B1 | 3/2004 | Sadler et al. |
| 6,719,766 B1 | 4/2004 | Buelna et al. |
| 6,780,195 B2 | 8/2004 | Porat |
| 6,824,547 B2 | 11/2004 | Wilson et al. |
| 6,843,253 B2 | 1/2005 | Parkes |
| 6,863,675 B2 | 3/2005 | Wilson, Jr. |
| 6,880,699 B2 | 4/2005 | Gallagher |
| 6,989,017 B2 | 1/2006 | Howell et al. |
| 7,001,412 B2 | 2/2006 | Gallagher et al. |
| 7,052,504 B2 | 5/2006 | Hughett |
| 7,107,995 B2 | 9/2006 | Parkes |
| 7,131,977 B2 | 11/2006 | Fowler |
| 7,211,091 B2 | 5/2007 | Fowler et al. |
| 7,211,092 B2 | 5/2007 | Hughett |
| 7,316,696 B2 | 1/2008 | Wilson et al. |

(56) References Cited

U.S. PATENT DOCUMENTS

| | | |
|---|---|---|
| 7,326,223 B2 | 2/2008 | Wilson, Jr. |
| 7,329,266 B2 | 2/2008 | Royse et al. |
| 7,402,164 B2 | 7/2008 | Watson et al. |
| 7,585,304 B2 | 9/2009 | Hughett |
| 7,635,374 B2 | 12/2009 | Monassevitch et al. |
| 7,645,285 B2 | 1/2010 | Cosgrove et al. |
| 7,892,244 B2 | 2/2011 | Monassevitch et al. |
| 7,963,964 B2 | 6/2011 | Santilli et al. |
| 7,992,757 B2 | 8/2011 | Wheeler et al. |
| 8,137,368 B2 | 3/2012 | Kayan et al. |
| 8,262,639 B2 | 9/2012 | Mathias |
| 8,465,507 B2 | 6/2013 | Cosgrove et al. |
| 8,517,970 B2 | 8/2013 | Mathias et al. |
| 8,795,302 B2 | 8/2014 | Wild |
| 8,945,151 B2 | 2/2015 | Salas |
| 8,945,157 B2 | 2/2015 | Gordon et al. |
| 9,084,596 B2 | 7/2015 | Stanley et al. |
| 9,119,627 B2 | 9/2015 | Cosgrove et al. |
| 9,220,507 B1 | 12/2015 | Patel et al. |
| 9,271,737 B2 | 3/2016 | Castro et al. |
| 9,282,972 B1 | 3/2016 | Patel et al. |
| 9,445,820 B2 | 9/2016 | Whiting |
| 9,456,824 B2 | 10/2016 | Willett et al. |
| 9,480,480 B2 | 11/2016 | Santilli et al. |
| 9,486,225 B2 | 11/2016 | Michler et al. |
| 9,855,053 B2 | 1/2018 | Bagaoisan et al. |
| 9,901,352 B2 | 2/2018 | Fago et al. |
| 10,130,373 B2 | 11/2018 | Castro et al. |
| 10,136,898 B2 | 11/2018 | Schmidt et al. |
| 10,201,353 B2 | 2/2019 | Menn |
| 10,258,345 B2 | 4/2019 | Brown |
| 10,265,079 B2 | 4/2019 | Brodaczewski et al. |
| 10,285,712 B2 | 5/2019 | Cosgrove et al. |
| 10,307,166 B2 | 6/2019 | Willett et al. |
| 10,327,762 B2 | 6/2019 | Lear |
| 10,335,157 B2 | 7/2019 | Patel et al. |
| 10,383,637 B2 | 8/2019 | Castro |
| 10,384,049 B2 | 8/2019 | Stanton et al. |
| 10,426,488 B2 | 10/2019 | Michler et al. |
| 10,542,998 B2 | 1/2020 | Whiting |
| 10,548,609 B2 | 2/2020 | Ramsey et al. |
| 10,687,822 B2 | 6/2020 | Bachar |
| 10,722,235 B2 | 7/2020 | Baril et al. |
| 10,729,448 B2 | 8/2020 | Patel et al. |
| 10,758,243 B2 | 9/2020 | Salas |
| 10,820,909 B2 | 11/2020 | Bagaoisan et al. |
| 10,881,414 B2 | 1/2021 | Lebens, III |
| 10,925,616 B2 | 2/2021 | Shellenberger et al. |
| 10,932,788 B2 | 3/2021 | Thomas et al. |
| 10,932,789 B2 | 3/2021 | Thomas et al. |
| 10,945,740 B2 | 3/2021 | Foshee et al. |
| 11,179,161 B1 | 11/2021 | Ambro |
| 11,246,600 B1 | 2/2022 | Brown |
| 11,291,459 B2 | 4/2022 | Ramsey et al. |
| 11,304,704 B2 | 4/2022 | Thomas et al. |
| 11,576,680 B2 | 2/2023 | Ramsey et al. |
| 11,992,222 B2 | 5/2024 | Shellenberger et al. |
| 2001/0049540 A1 | 12/2001 | Santilli |
| 2002/0068946 A1 | 6/2002 | Kortenbach et al. |
| 2002/0111640 A1 | 8/2002 | Krause et al. |
| 2002/0169459 A1 | 11/2002 | Porat |
| 2002/0183785 A1 | 12/2002 | Howell et al. |
| 2003/0074009 A1 | 4/2003 | Ramsey et al. |
| 2003/0236537 A1 | 12/2003 | Hart et al. |
| 2004/0059359 A1 | 3/2004 | Wilson |
| 2004/0112392 A1 | 6/2004 | Parkes |
| 2004/0129277 A1 | 7/2004 | Parkes |
| 2004/0172043 A1 | 9/2004 | Watson et al. |
| 2005/0033333 A1 | 2/2005 | Smith et al. |
| 2005/0149069 A1 | 7/2005 | Bertolero et al. |
| 2005/0165421 A1 | 7/2005 | Wilson et al. |
| 2005/0165422 A1 | 7/2005 | Wilson, Jr. |
| 2005/0165423 A1 | 7/2005 | Gallagher et al. |
| 2005/0165424 A1 | 7/2005 | Gallagher et al. |
| 2005/0165429 A1 | 7/2005 | Douglas et al. |
| 2005/0273122 A1 | 12/2005 | Theroux et al. |
| 2005/0277959 A1 | 12/2005 | Cosgrove et al. |
| 2006/0100649 A1 | 5/2006 | Hart |
| 2006/0129170 A1 | 6/2006 | Royce et al. |
| 2006/0200179 A1 | 9/2006 | Barker et al. |
| 2006/0217749 A1 | 9/2006 | Wilson et al. |
| 2007/0016228 A1 | 1/2007 | Salas |
| 2007/0083218 A1 | 4/2007 | Steven |
| 2007/0118161 A1 | 5/2007 | Kennedy et al. |
| 2007/0149988 A1 | 6/2007 | Michler et al. |
| 2007/0149989 A1 | 6/2007 | Santilli et al. |
| 2007/0173866 A1 | 7/2007 | Sorrentino et al. |
| 2007/0213585 A1 | 9/2007 | Monassevitch et al. |
| 2007/0213747 A1 | 9/2007 | Monassevitch et al. |
| 2007/0276417 A1 | 11/2007 | Mendes et al. |
| 2008/0039879 A1 | 2/2008 | Chin et al. |
| 2008/0045981 A1 | 2/2008 | Margolin et al. |
| 2008/0103512 A1 | 5/2008 | Gately |
| 2008/0208324 A1 | 8/2008 | Glithero et al. |
| 2008/0287976 A1 | 11/2008 | Weaner et al. |
| 2008/0312670 A1 | 12/2008 | Lutze et al. |
| 2009/0012545 A1 | 1/2009 | Williamson et al. |
| 2009/0088783 A1 | 4/2009 | Kennedy et al. |
| 2009/0088786 A1 | 4/2009 | Zook et al. |
| 2009/0171380 A1 | 7/2009 | Whiting |
| 2009/0240266 A1 | 9/2009 | Dennis |
| 2009/0306619 A1 | 12/2009 | Mathias et al. |
| 2010/0082047 A1 | 4/2010 | Cosgrove et al. |
| 2010/0114131 A1 | 5/2010 | Rotunda |
| 2010/0211080 A1 | 8/2010 | Trivisani et al. |
| 2010/0274268 A1 | 10/2010 | Singh et al. |
| 2010/0331862 A1 | 12/2010 | Monassevitch et al. |
| 2011/0022079 A1 | 1/2011 | Miles et al. |
| 2011/0112559 A1 | 5/2011 | Monassevitch et al. |
| 2011/0245848 A1 | 10/2011 | Rosenberg et al. |
| 2011/0270285 A1 | 11/2011 | Lissa |
| 2011/0295291 A1 | 12/2011 | Trivisani |
| 2012/0027804 A1 | 2/2012 | Odermatt et al. |
| 2012/0083803 A1 | 4/2012 | Patel et al. |
| 2012/0312858 A1 | 12/2012 | Patankar et al. |
| 2013/0006271 A1 | 1/2013 | Vold et al. |
| 2013/0226200 A1 | 8/2013 | Kappel et al. |
| 2013/0245651 A1 | 9/2013 | Schmidt et al. |
| 2013/0245652 A1 | 9/2013 | Cosgrove et al. |
| 2013/0245653 A1 | 9/2013 | Litherland |
| 2013/0253540 A1 | 9/2013 | Castro et al. |
| 2013/0261642 A1 | 10/2013 | Willett et al. |
| 2013/0289588 A1 | 10/2013 | Robertson et al. |
| 2014/0018832 A1 | 1/2014 | Shelton, IV |
| 2014/0058411 A1 | 2/2014 | Soutorine et al. |
| 2014/0236170 A1 | 8/2014 | Kethman et al. |
| 2014/0243862 A1 | 8/2014 | Bagaoisan et al. |
| 2015/0066064 A1 | 3/2015 | Kubiak |
| 2015/0127027 A1 | 5/2015 | Vandewalle |
| 2015/0190137 A1 | 7/2015 | Salas |
| 2015/0320426 A1 | 11/2015 | Cosgrove et al. |
| 2016/0053926 A1 | 2/2016 | Whitaker |
| 2016/0151073 A1 | 6/2016 | Castro et al. |
| 2016/0174981 A1 | 6/2016 | Fago et al. |
| 2016/0262756 A1 | 9/2016 | Patankar et al. |
| 2016/0354089 A1 | 12/2016 | Whiting |
| 2017/0009895 A1 | 1/2017 | Stanton et al. |
| 2017/0014124 A1 | 1/2017 | Lear |
| 2017/0020530 A1 | 1/2017 | Willett et al. |
| 2017/0027576 A1 | 2/2017 | Castro |
| 2017/0065280 A1 | 3/2017 | Micher et al. |
| 2017/0209151 A1 | 7/2017 | Brown |
| 2017/0232247 A1 | 8/2017 | Sonderegger et al. |
| 2017/0311954 A1 | 11/2017 | Brodaczewski et al. |
| 2017/0325818 A1 | 11/2017 | Trivisani |
| 2018/0036008 A1 | 2/2018 | Ramsey et al. |
| 2018/0146965 A1 | 5/2018 | Bachar |
| 2018/0168659 A1 | 6/2018 | Bagaoisan et al. |
| 2018/0185029 A1 | 7/2018 | Lebens, III |
| 2018/0221029 A1 | 8/2018 | Menn |
| 2018/0271527 A1 | 9/2018 | Shellenberger |
| 2018/0271532 A1 | 9/2018 | Shellenberger |
| 2018/0271535 A1 | 9/2018 | Shellenberger et al. |
| 2018/0271536 A1 | 9/2018 | Shellenberger et al. |

(56) References Cited

U.S. PATENT DOCUMENTS

| | | |
|---|---|---|
| 2018/0344321 A1 | 12/2018 | Soutorine et al. |
| 2018/0368852 A1 | 12/2018 | Foshee et al. |
| 2019/0072217 A1 | 3/2019 | Whitaker |
| 2019/0231352 A1 | 8/2019 | Maekubo |
| 2019/0314025 A1 | 10/2019 | Patel et al. |
| 2019/0314026 A1 | 10/2019 | Thomas et al. |
| 2019/0314031 A1 | 10/2019 | Thomas et al. |
| 2020/0008810 A1 | 1/2020 | Patel et al. |
| 2020/0046359 A1 | 2/2020 | Thomas et al. |
| 2020/0155158 A1 | 5/2020 | Whiting |
| 2020/0170645 A1 | 6/2020 | Ramsey et al. |
| 2020/0352574 A1 | 11/2020 | Ramsey et al. |
| 2020/0360021 A1 | 11/2020 | Foshee |
| 2020/0405315 A1 | 12/2020 | Zhang et al. |
| 2021/0045745 A1 | 2/2021 | Bagaoisan et al. |
| 2021/0128159 A1 | 5/2021 | Taylor et al. |
| 2021/0186511 A1 | 6/2021 | Shellenberger et al. |
| 2021/0228212 A1 | 7/2021 | Lebens, III |
| 2021/0267603 A1 | 9/2021 | Foshee et al. |
| 2021/0267604 A1 | 9/2021 | Enniss |
| 2021/0298758 A1 | 9/2021 | Thomas et al. |
| 2021/0346028 A1 | 11/2021 | Brodaczewski et al. |
| 2022/0047266 A1 | 2/2022 | Brown |
| 2022/0047269 A1 | 2/2022 | Castro |

FOREIGN PATENT DOCUMENTS

| | | |
|---|---|---|
| CN | 102028517 A | 4/2011 |
| CN | 102860850 A | 1/2013 |
| CN | 103919589 A | 7/2014 |
| CN | 104039247 A | 9/2014 |
| CN | 105054989 A | 11/2015 |
| CN | 105387298 A | 3/2016 |
| CN | 105534558 A | 5/2016 |
| CN | 105682569 A | 6/2016 |
| CN | 106264646 A | 1/2017 |
| EP | 0086640 A2 | 8/1983 |
| EP | 0122046 A1 | 10/1984 |
| EP | 0201344 A2 | 11/1986 |
| EP | 0314064 A2 | 5/1989 |
| EP | 0635241 A2 | 1/1995 |
| EP | 1233705 A2 | 8/2002 |
| EP | 2074954 A1 | 7/2009 |
| EP | 3493747 A1 | 6/2019 |
| EP | 3552561 A2 | 10/2019 |
| GB | 2025511 A | 1/1980 |
| GB | 2054027 A | 2/1981 |
| GB | 2069848 A | 9/1981 |
| GB | 2353710 A | 3/2001 |
| GB | 2465560 A | 5/2010 |
| JP | 56-151034 A | 11/1981 |
| JP | 58-041541 A | 3/1983 |
| JP | 58-146341 A | 8/1983 |
| JP | 61-259652 A | 11/1986 |
| JP | 01-146536 A | 6/1989 |
| JP | 03-178648 A | 8/1991 |
| JP | 05-176936 A | 7/1993 |
| JP | 2002-345828 A | 12/2002 |
| JP | 2006-515529 A | 6/2006 |
| JP | 2008-543354 A | 12/2008 |
| JP | 2014-504185 A | 2/2014 |
| JP | 2014-534014 A | 12/2014 |
| KR | 10-1991-0007490 A | 5/1991 |
| KR | 10-2016-0115163 A | 10/2016 |
| WO | 01/35837 A1 | 5/2001 |
| WO | 01/37742 A2 | 5/2001 |
| WO | 2004/043225 A2 | 5/2004 |
| WO | 2005/074420 A2 | 8/2005 |
| WO | 2005/074421 A2 | 8/2005 |
| WO | 2006/102578 A1 | 9/2006 |
| WO | 2012/075532 A1 | 6/2012 |
| WO | 2016/094647 A1 | 6/2016 |
| WO | 2016/205343 A1 | 12/2016 |
| WO | 2017/017587 A2 | 2/2017 |
| WO | 2018/027032 A1 | 2/2018 |
| WO | 2018/196935 A1 | 11/2018 |
| WO | 2018/237277 A1 | 12/2018 |
| WO | 2019/099462 A1 | 5/2019 |
| WO | 2019/169580 A1 | 9/2019 |
| WO | 2020/102700 A1 | 5/2020 |

OTHER PUBLICATIONS

Ebbinghaus, M., European Search Report, EP 12842249, Mar. 9, 2015, 7 pages, EPO.

English translation of Notice of Reasons for Rejection issued in Japanese Patent Application No. 2014-537368, dated Sep. 15, 2016.

Examiner's Report issued in Japanese Application No. 2014-537368, dated Feb. 6, 2018.

International Preliminary Report on Patentability and Written Opinion issued in PCT/US2018/060946, dated May 28, 2020.

International Preliminary Report on Patentability and Written Opinion issued in PCT/US2019/061767, dated May 27, 2021.

International Search Report and Written Opinion issued in PCT/US2019/061767, dated Jan. 13, 2020.

International Search Report and Written Opinion issued in PCT/US2020/066178, dated Apr. 6, 2021.

International Search Report from PCT/US2018/060946; dated Feb. 6, 2019.

Jung, Soo Hwan, International Search Report, PCT/US2012/061384, dated Mar. 29, 2013, 5 pages, KIPO.

Office Action issued in European Application No. 17199789.3, dated Apr. 16, 2018.

Office Action issued in European Application No. 17199789.3, dated Apr. 5, 2018.

Office Action issued in European Application No. 17199790.1, dated Apr. 16, 2018.

Office Action issued in European Application No. 17199790.1, dated Mar. 1, 2018.

Search Report issued in European Application No. 17199790.1, dated Feb. 20, 2018.

SURGICAL CLIP

CROSS-REFERENCE TO RELATED APPLICATIONS

This application is a continuation of U.S. patent application Ser. No. 18/196,979, filed on May 12, 2023, which is a continuation of U.S. patent application Ser. No. 16/762,442, filed on May 7, 2020, now U.S. Pat. No. 11,648,014, which is a National Stage Entry of International Patent Application No. PCT/US2018/060946, filed on Nov. 14, 2018, which claims priority from U.S. Provisional Patent Application No. 62/585,795, filed on Nov. 14, 2017, each titled "SURGICAL CLIP", and the disclosures of each application are incorporated by reference in their entirety.

TECHNICAL FIELD

The present invention relates generally to medical devices, and more particularly, to surgical clips for ligation of tissue.

BACKGROUND

The ligation of tissue (e.g., blood vessels, lymph nodes, nerves, fallopian tubes, or cardiac tissue) is a common practice of many surgical procedures. For example, the temporary ligation of blood vessels (e.g., veins or arteries) is often required during the resection of the blood vessels to remove an aneurysm. On the other hand, the ligation of fallopian tubes is often desired to be more permanent. Ligation clips are relatively quick and easy to apply, so they have grown in popularity.

Overview

The present inventors recognize that there is a need to improve one or more features of the ligation clips. Current ligation clips often do not provide sufficient strength to ensure that the clip remains closed during its intended use. This is especially problematic with ligation clips formed of absorbable materials, which can be substantially weaker than non-absorbable materials. The weaker materials may potentially lead the implanted surgical clip to wear and/or break, causing the ligation clip to open. For example, uneven absorption and/or degradation of the material can cause the ligation clip to open prior to the desired tissue necrosis of vascular tissue. It would be desirable to provide a ligation clip having an improved locking mechanism to ensure that the clip remains closed during its intended use. The disclosed ligation clips are directed to mitigating or overcoming one or more of these problems.

A first aspect of the present invention is directed to a surgical clip configured to ligate tissue. The surgical clip may include a first leg member and a second leg member. The first leg member may include an inner surface with a concave curvature along its length, and the second leg member may have an inner surface with a convex curvature along its length. The first and second leg members may be configured to move between an open configuration wherein the inner surfaces are spaced apart and a closed configuration wherein the inner surfaces are approximated. The surgical clip may have a first locking member positioned on a distal end portion of the first leg member, and a second locking member positioned on a distal end portion of the second leg member, the first and second locking members being configured to interact to secure the first and second leg members in the closed configuration. The surgical clip may also include a third locking member position between a proximal end portion and the distal end portion of the first leg member, and a fourth locking member positioned between a proximal end portion and the distal end portion of the second leg member, the third and fourth locking members being configured to interact to secure the first and second leg members in the closed configuration.

In some embodiments, the first locking member includes a hook and the second locking member includes a recess, where the hook is configured to deflect around the distal end portion of the second leg member and snap into the recess. In some embodiments, the third locking member includes an elongate member having a protrusion, and the fourth locking member includes a channel having an undercut, where the channel is configured to receive the elongate member and the undercut is configured to engage the protrusion. In some embodiments, the protrusion is spaced from the undercut in the closed configuration. In some embodiments, the third locking member be a single protrusion without a ratcheting mechanism. In some embodiments, the channel extends through a first segment of the second leg member, the first segment having a width greater than a width of a second segment of the second leg member. In some embodiments, the second segment of the second leg member is configured to engage tissue. In some embodiments, the third locking member is arcuate. In some embodiments, the third locking member includes an atraumatic end. In some embodiments, the third locking member is positioned on a proximal half of the inner surface of the first leg member. In some embodiments, a hinge portion connecting the proximal end portions of the first and second leg members, the hinge portion being configured to pivot the first leg member relative to the second leg member. In some embodiments, the third locking member forms a portion of a hinge portion connecting the proximal end portions of the first and second leg members. In some embodiments, the hinge portion includes a barrel positioned on the proximal end of the first leg member configured to rotate about a hinge pin positioned on the proximal end portion of the second leg member, the barrel including the third locking member. In some embodiments, the third locking member includes a protrusion on the barrel, and the fourth locking member is an undercut in the proximal end portion of the second leg member. In some embodiments, the protrusion is spaced from the undercut in the closed configuration. In some embodiments, the barrel includes an opening between an end of the third locking member and a proximal end portion of the first leg member, and the hinge pin includes at least one flat surface, wherein the opening is substantially offset from the flat surface when the surgical clip is in the closed configuration. In some embodiments, the at least one flat surface is disposed at angle of about 135° from a longitudinal axis of the second leg member. In some embodiments, the surgical clip includes a boss positioned on the distal end portion of at least one of the first and second leg members. In some embodiments, the clip includes an absorbable polymer material. In some embodiments, the at least one of the inner surfaces of the first and second leg members includes a plurality of teeth angled toward a proximal end portion of the surgical clip. In some embodiments, both of the inner surfaces of the first and second leg members include a plurality of teeth angled toward the proximal end portion of the clip. In some embodiments, the plurality of teeth are positioned distal of the third locking member. In some embodiments, the third locking member includes first and second elongate members extending from opposing side surfaces of the first leg member, and the fourth locking member includes an outer surface of the second leg member.

In some embodiments, the first and second elongate members includes a protrusion configured to engage the outer surface of the second leg member.

BRIEF DESCRIPTION OF THE DRAWINGS

In order that the invention may be readily understood, aspects of this invention are illustrated by way of examples in the accompanying drawings.

The same reference numbers are used in the drawings and the following detailed description to refer to the same or similar parts.

DETAILED DESCRIPTION

Figure 1:
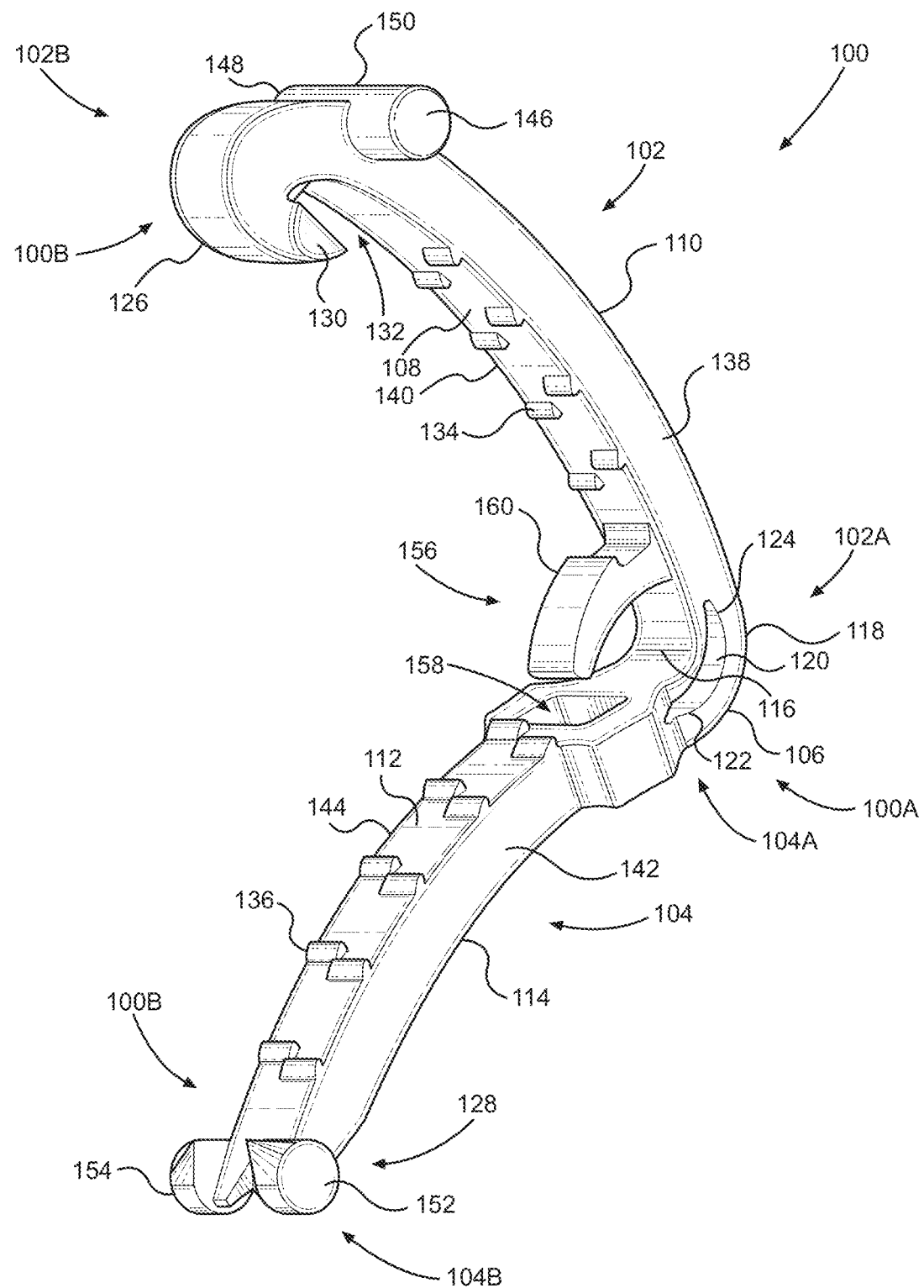
FIG. 1 illustrates a perspective view of a first exemplary embodiment of a surgical clip of the present invention.

The present invention is generally directed to a surgical clip configured to ligate tissue (e.g., a blood vessel). The surgical clip may include first and second leg members configured to pivot between an open configuration and a closed configuration. The surgical clip may also have first and second locking mechanisms along the length of surgical clip to provide strength and ensure that the clip remains in the closed configuration. For example, the surgical clip may include a first latching or locking mechanism on a distal end portion of the surgical clip, and a second latching or locking mechanism between the distal end portion and a proximal end portion. Each of the first and second locking mechanisms may include latching, interlocking, and/or interfering members that collectively secure the surgical clip in the closed configuration. For example, the first locking mechanism may include a hook on the first leg member configured to deflect around a tip member on the second leg member. The second locking mechanism may include one or more arcuate elongate member on the first leg member configured to engage the second leg member. In some embodiments, the arcuate elongate member may pass through a channel in the second leg member and produce an interference fit with an undercut of the channel when in the closed configuration. In some embodiments, the second locking mechanism may include a portion of a barrel of a hinge portion of the first leg member, and the barrel may be configured to releasably receive a pivot pin of the second leg member. In some embodiments, the second locking member may include first and second arcuate elongate members extending from side surfaces of the first leg member and configured to engage an outer surface of the second leg member. The second locking mechanism may include interfering members (e.g., the elongate member(s) and/or a surface of the second leg member) spaced apart from each other in the closed configuration to allow for flexibility along the length of the surgical clip and/or to accommodate for different thicknesses of tissue, while reinforcing the first locking mechanism. The surgical clip may be particularly useful as a hemostatic clip configured to be latched around a vessel to thereby reduce and/or stop the flow of fluid through the vessel. However, it is also contemplated that the embodiments of the surgical clip may have non-surgical applications, such as to clasp hair.

The invention will now be described with reference to the figures, in which like reference numerals refer to like parts throughout. In accordance with conventional practice, as used herein, and unless otherwise indicated herein, the term "proximal end portion" refers to the specified end portion of the surgical clip and/or related component which is generally closer to the medical personnel handling or manipulating the device as it is intended to be used, and the term "distal end portion" shall refer to the specified end portion of the surgical clip and/or related component which is opposite the proximal end portion. As used herein, the term "longitudinal" is directed to the dimension which extends along the length of the surgical clip and/or related components, as would be commonly understood by one of skill in the art. Furthermore, as used herein, the term "transverse" is directed to any axis or direction which is orthogonal to the longitudinal length of the surgical clip and/or related components.

FIGS. 1-4 illustrate a first exemplary embodiment of a surgical clip 100 of the present invention. The surgical clip 100 may have a proximal end portion 100A and a distal end portion 100B. The surgical clip 100 may further include a first leg member 102 having a proximal end portion 102A and a distal end portion 102B, and a second leg member 104 having a proximal end portion 104A and a distal end portion 104B. The proximal end portions 102A, 104A may be connected by a hinge portion 106.

The first and second leg members 102, 104 may include surfaces having curved portions. For example, the first leg member 102 may include a first inner surface 108 and a first outer surface 110, and the second leg member 104 may include a second inner surface 112 and a second outer surface 114. As shown in FIG. 1, the first inner surface 108 may have a concave configuration, and the first outer surface 110 may have a convex configuration, or vice versa. The second inner surface 112 may have a convex configuration, and the second outer surface 114 may have a concave configuration, or vice versa. The first and second inner surfaces 108, 112 may be approximated in a closed configuration, and may be resiliently flexible along its length to distribute pressure over a width of the tissue as the tissue is ligated. The first and second inner surfaces 108, 112 may each have a continuous curvature between proximal and distal end portions to provide a favorable compression of tissue.

The hinge portion 106 may have a concave inner surface 116 and a convex outer surface 118. The concave inner surface 116 of hinge portion 106 may continuously join the first inner surface 108 of the first leg member 102 and the second inner surface 112 of the second leg member 104. The convex outer surface 118 of the hinge portion 106 may join the first outer surface 110 of the first leg member 102 and the second outer surface 114 of the second leg member 104. The hinge portion 106 may also include a curved slot 120 located between the curved hinge surfaces 116, 118, and the curved slot 120 may be positioned closer to the concave inner surface 116 than to the convex outer surface 118. The curved slot 120 may extend completely through the hinge portion 106 from side to side and its opposite ends 122, 124 may extend into the proximal end portions 102A, 104A of the first and second leg members 102, 104, respectively. The curved slot 120 may provide added flexibility and resiliency to the hinge portion 106, but the concave inner surface 116 may prevent any portion of a clamped vessel from being trapped within the curved slot 120. In some embodiments, the hinge portion 106 may be resilient and integral to the proximal end portions 102A, 104A of the first and second leg members 102, 104. For example, the hinge portion 106 may bias the surgical clip 100 into an open configuration (e.g., FIG. 1).

The surgical clip 100 may also include one or more latching or locking mechanisms. For example, the first leg member 102 may transition to a hook section 126 at its distal end portion 102B, and the second leg member 104 may transition to a pointed tip portion 128 at its distal end 104B. A distal end portion of the hook section 126 may curve inwardly and point generally toward the concave inner surface 116 of the hinge portion 106. The hook section 126 may have one or more transverse beveled surfaces 130 and a concave inner surface which merges with the first inner surface 108 to define a recess 132. The tip portion 128 may be V-shaped defining a slot configured to receive the beveled surfaces 130, as the hook section 126 deflects around the tip portion 128. The hook section 126 and the tip portion 128 may engage to form a first latching or locking mechanism. For example, the recess 132 may engage with the tip portion 128 in the course of compressing the surgical clip 100 into the closed configuration (e.g., FIGS. 3-4) that may be secured position around a vessel or other tissue.

The surgical clip 100 may also include a second latching or locking mechanism. For example, as depicted in FIGS. 1-4, an elongate member 156 may extend from the first inner surface 108 of the first leg member 102, between the proximal end portion 102A and the distal end portion 102B. The elongate member 156 may be positioned anywhere on the length of the first leg member 102. In some embodiments, the elongate member 156 may be positioned closer to the proximal end portion 102A than the distal end portion 102B (e.g., on the proximal half of the first leg member 102) in order to secure the proximal end portion 100A of the surgical clip 100. In some embodiments, the elongate member 156 may be positioned closer to the proximal end portion 102A than a centerline of the first leg member 102 (e.g., on the proximal quarter of the first leg member 102) in order to distribute the latching force along the length of the surgical clip 100. The elongate member 156 may extend in an arcuate configuration from the first leg member 102 approximating the arcuate path of the second leg member 104 relative to the first leg member 102. When the surgical clip 100 is in the closed configuration (e.g., FIGS. 3-4), the elongate member 156 may be received in an aperture or channel 158 through at least a portion of the thickness of the second leg member 104. As depicted in FIG. 1, the channel 158 may have a width substantially equal to or greater than a width of the remaining portion of the second leg member 104, such that the width of the portion of second leg member 104 through which the channel 158 extends may be greater than the width of the remaining portion of the second leg member 104 configured to engage tissue. Although FIGS. 1-4 illustrate the elongate member 156 on the first leg member 102 and the channel 158 on the second leg member 104, the surgical clip 100 may, additionally or alternatively, include an elongated member 156 on the second leg member 104 and a channel 158 on the first leg member 102. It is further contemplated that the surgical clip 100 may include a plurality of elongated members 156 on the first leg member 102 and/or second leg member 104 and a plurality of corresponding channels 158 on the opposite leg member 102, 104.

Figure 2:
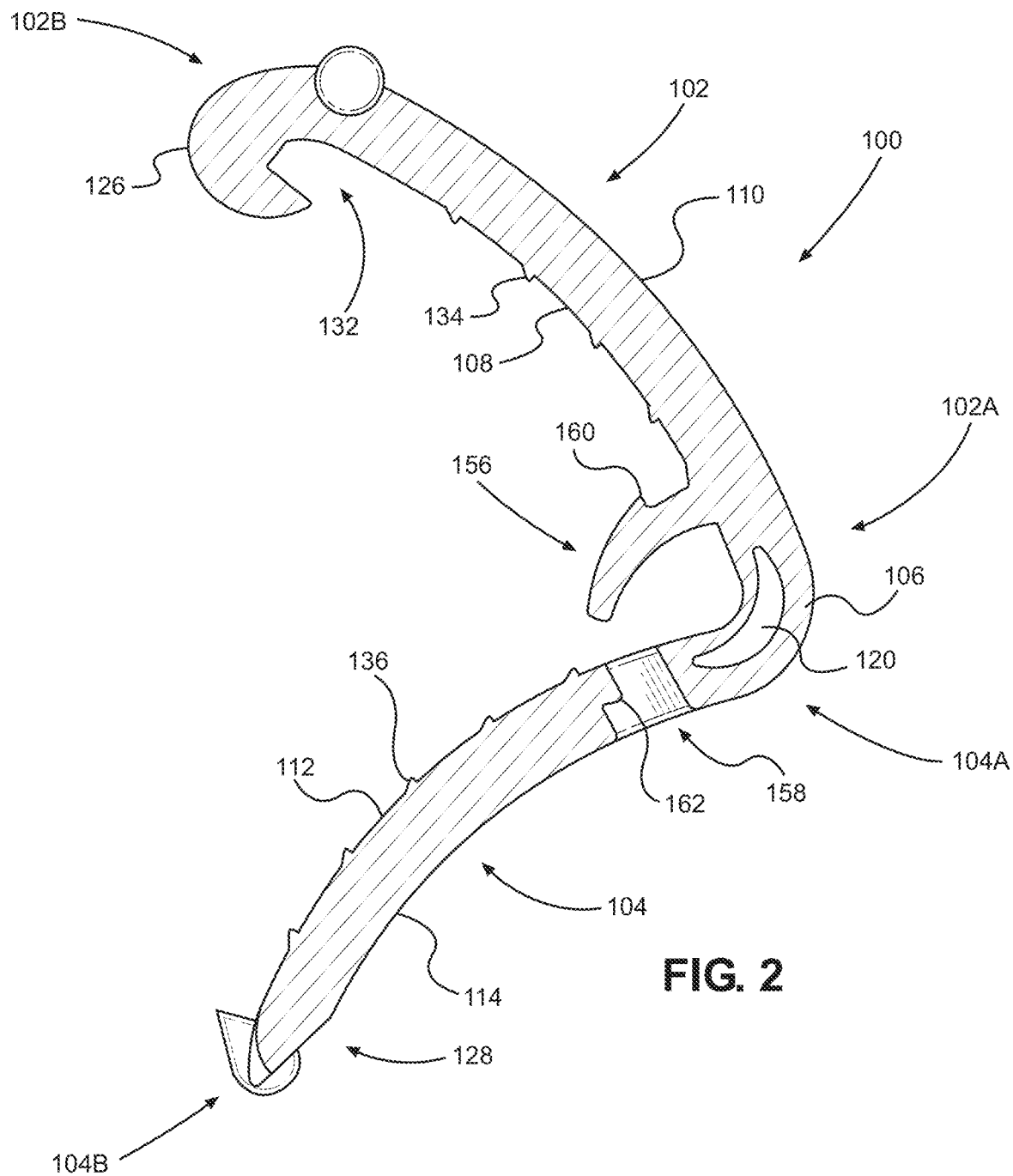
FIG. 2 illustrates a cross-sectional view of the first exemplary embodiment of the surgical clip of FIG. 1.
Figure 3:
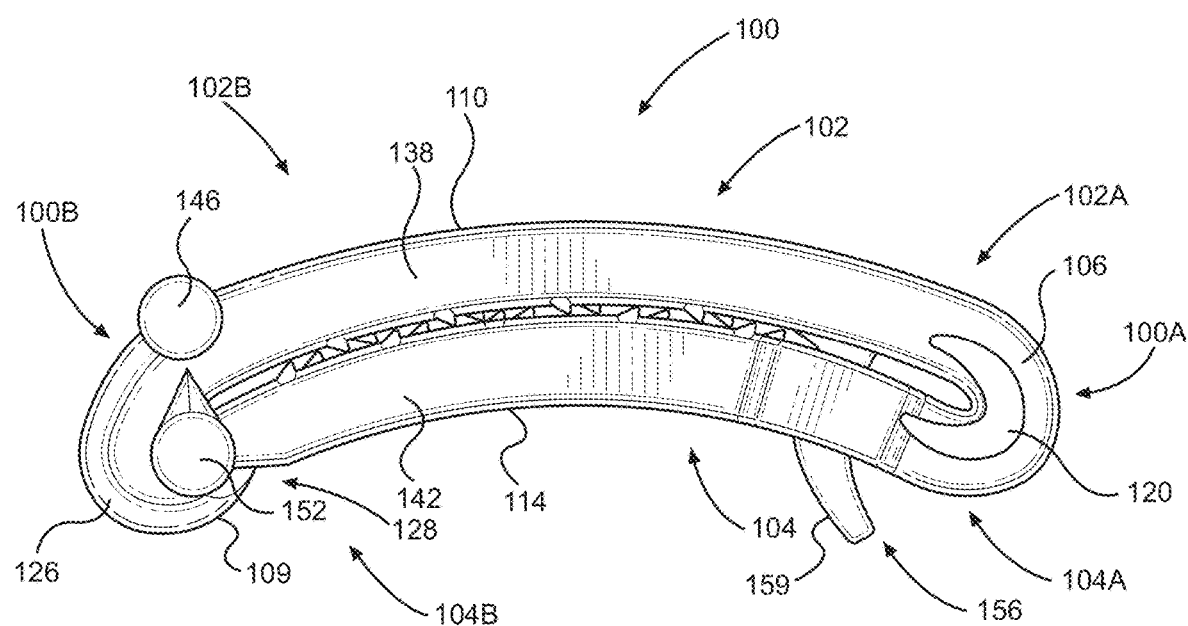
FIG. 3 illustrates a closed configuration of the first exemplary embodiment of the surgical clip of FIGS. 1 and 2.
Figure 4:
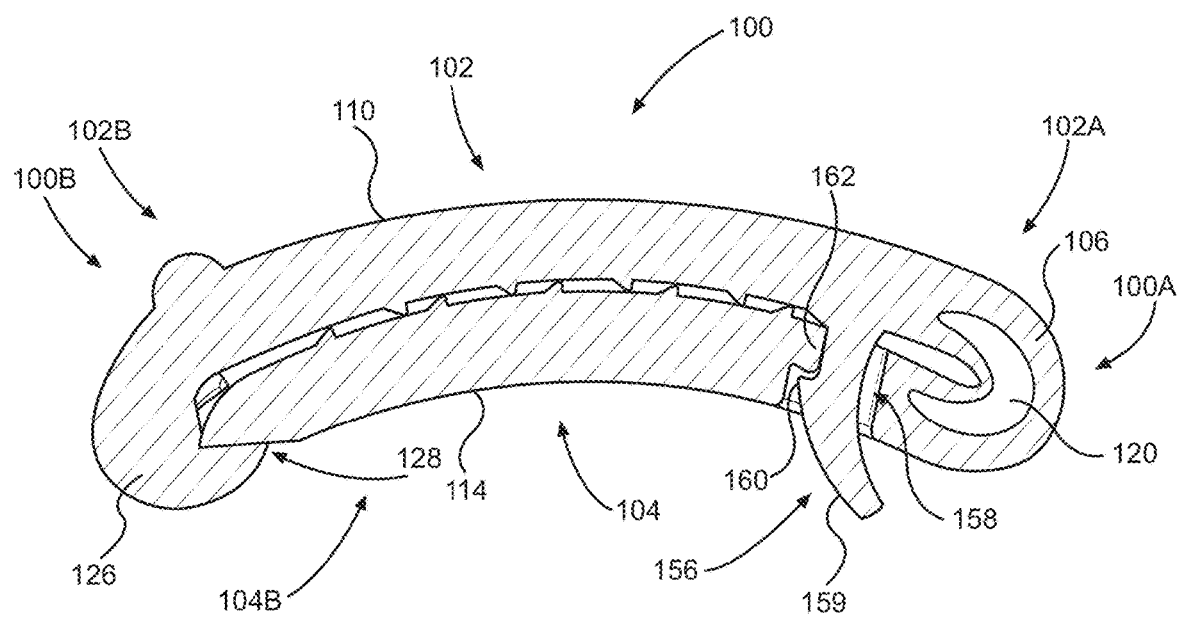
FIG. 4 illustrates a cross-sectional view of the closed configuration of the first exemplary embodiment of the surgical clip of FIGS. 1-3.

As further depicted in the cross-sectional views of FIGS. 2 and 4, the elongate member 156 may include a tooth or protrusion 160 configured to engage an undercut 162 of the channel 158 to provide the second latching or locking mechanism. The protrusion 160 may be spaced from the undercut 162 when the surgical clip 100 is in the closed configuration and in the absence of tissue (e.g., FIGS. 3-4). For example, the first locking mechanism may be engaged in the closed configuration, while the second locking mechanism may not be engaged. The spacing between the protrusion 160 and undercut 162 in the closed configuration may allow flexibility of the surgical clip 100 along its length to accommodate different thicknesses of tissue and to distribute pressure over a width of the tissue as it is ligated. The second locking mechanism may also reinforce the first locking mechanism. For example, the second locking mechanism may prevent the surgical clip 100 from opening when the surgical clip 100 (e.g., the first locking mechanism) wears and/or breaks, such as when uneven absorption and/or degradation of the surgical clip 100 causes the first locking mechanism to disengage. In that sense, the elongate member 156 may include only a single protrusion 160, without any type of ratcheting or tightening mechanism.

It is contemplated that the channel 158 may extend through the entire thickness of the second leg member 104. The elongate member 156 may have a length greater than a length of the channel 158, in order to provide an exposed distal end portion 159 of the elongate member 156. The exposed distal end portion 159 of the elongate member 156 may be engaged and deflected proximally to release the second locking mechanism. The elongate member 156 may also be atraumatic with an atraumatic end and provide a stop to prevent the tissue from being pinched by the hinge portion 106.

As further shown in the embodiment of FIGS. 1 and 3, the surgical clip 100 may include a first plurality of teeth 134 protruding on the first inner surface 108, and a second plurality of teeth 136 protruding on the second inner surface 112. The teeth 134, 136 may maximize security of compressed tissue and minimize migration. The teeth 134, 136 may be angled toward the proximal end portion 102A of the surgical clip 100 in order to secure the tissue toward the hinge portion 106. As depicted in FIG. 1, the first and second plurality of teeth 134, 136 may include two or more staggered rows of teeth collectively extending the width of the inner surfaces 108, 112. As further depicted in FIGS. 3-4, the first plurality of teeth 134 may not engage the second plurality of teeth 136 in the closed configuration to increase the discrete contact points along the length of the surgical clip 100 and enhance security. In some embodiments, one or more of the teeth 134, 136 may be omitted.

The leg members 102, 104 may include one or more bosses along their length to engage a clip applier. For example, the first leg member 102 may include cylindrical bosses 146, 148 (e.g., as depicted in FIGS. 1 and 3) protruding perpendicular to each of the opposed side surfaces 138, 140 adjacent to distal end portion 102B of first leg member 102 and immediately inward of hook section 126. In the illustrated example of the surgical clip 100, the bosses 146, 148 may be cylindrical and project outwardly beyond the first outer surface 110 of first leg member 102. The bosses 146, 148 may also be coupled together by a bridge section 150. The second leg member 104 may also include bosses 152, 154 at the distal end portion 104B. The bosses 152, 154 may be cylindrical and protrude perpendicular to each of opposed side surfaces 142, 144 of second leg member 104, extending longitudinally forward beyond the point of tip portion 128. In the practice of ligating tissue, the surgical clip 100 may be designed to be compressed into a latched or locked configuration around the vessel through the use of an appropriate clip applier, such as described in U.S. Pat. No. 5,100,416, the entire disclosure of which is incorporated herein by reference.

FIGS. 5-8 illustrate a second exemplary embodiment of a surgical clip 200 of the present invention. The surgical clip 200 may have a proximal end portion 200A and a distal end portion 200B. The surgical clip 200 may further include a first leg member 202 having a proximal end portion 202A and a distal end portion 202B, and a second leg member 204 having a proximal end portion 204A and a distal end portion 204B. The proximal end portions 202A, 204A of the first and second leg members 202, 204 may be releasably connected at a hinge portion 206. The surgical clip 200 may have elements and/or aspects similar to the surgical clip 100, and may be similarly represented in FIGS. 5-8. For the sake of brevity, the elements and/or aspects similar to those of the surgical clip 100 may not be discussed with reference to the surgical clip 200.

The first and second leg members 202, 204 may include surfaces having curved portions. For example, the first leg member 202 may include a first inner surface 208 and a first outer surface 210, and the second leg member 204 may include a second inner surface 212 and a second outer surface 214. The first inner surface 208 may have a concave configuration, and the first outer surface 210 may have a convex configuration, or vice versa. The second inner surface 212 may have a convex configuration, and the second outer surface 214 may have a concave configuration, or vice versa. The first and second inner surfaces 208, 212 may be approximated in a closed configuration, and may be resiliently flexible along its length to distribute pressure over a width of the tissue as the tissue is ligated. The first and second inner surfaces 208, 212 may each have a continuous curvature between proximal and distal end portions to provide a favorable compression of tissue.

The surgical clip 200 may also include one or more latching or locking mechanisms. For example, the first leg member 202 may transition to a hook section 226 at its distal end portion 202B, and the second leg member 204 may transition to a pointed tip portion 228 at its distal end 204B. A distal end portion of the hook section 226 may curve inwardly and point generally toward the concave inner surface 216 of the hinge portion 206. The hook section 226 may have one or more transverse beveled surfaces 230 and a concave inner surface which merges with the first inner surface 208 to define a recess 232. The tip portion 228 may be V-shaped defining a slot configured to receive the beveled surfaces 230, as the hook section 226 deflects around the tip portion 228. The hook section 226 and the tip portion 228 may engage to form a first latching or locking mechanism. For example, the recess 232 may engage with the tip portion 228 in the course of compressing the surgical clip 200 into the closed configuration (e.g., FIGS. 7-8) that may be secured position around a vessel or other tissue.

Figure 5:
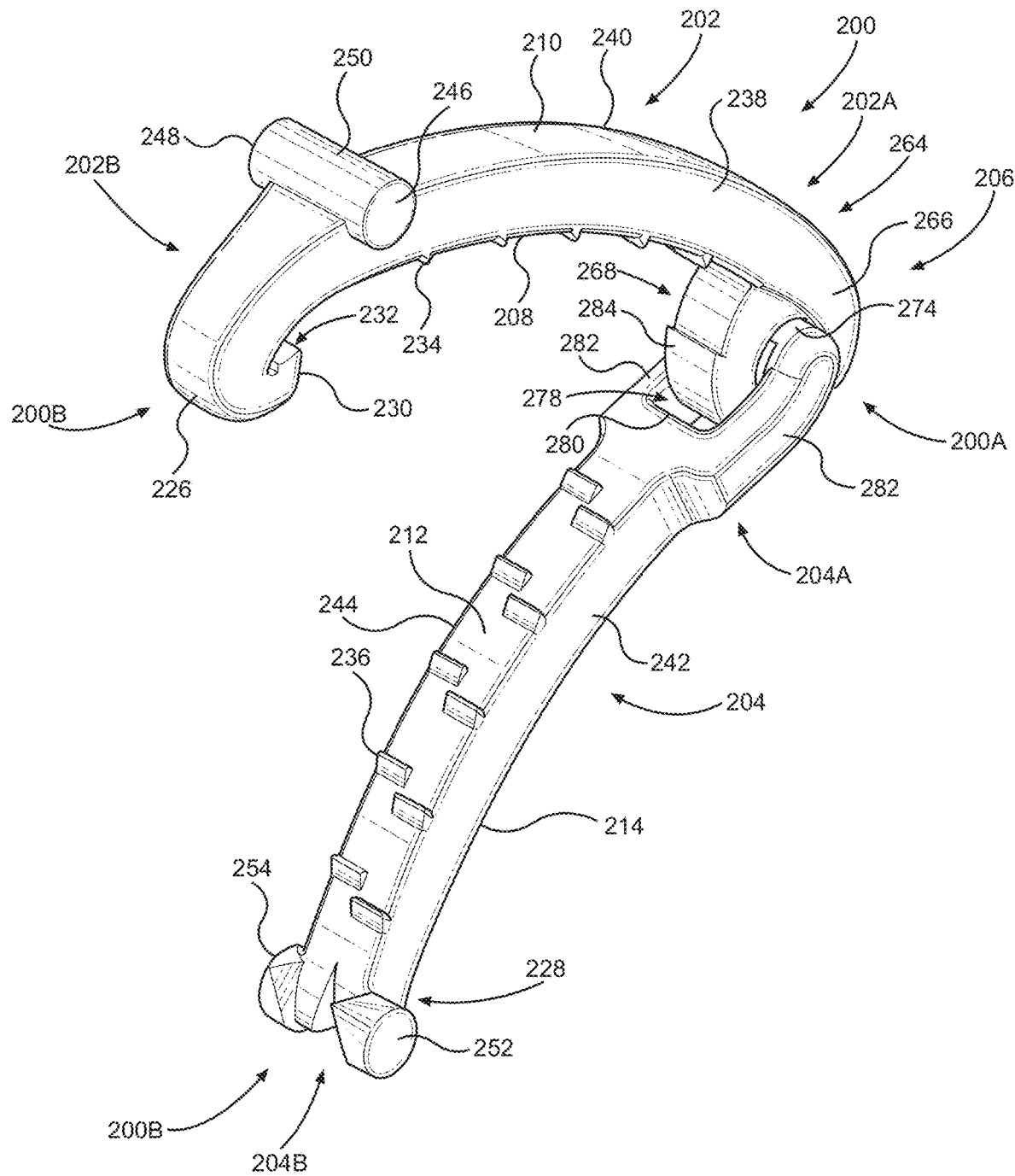
FIG. 5 illustrates a perspective view of a second exemplary embodiment of a surgical clip of the present invention.
Figure 6:
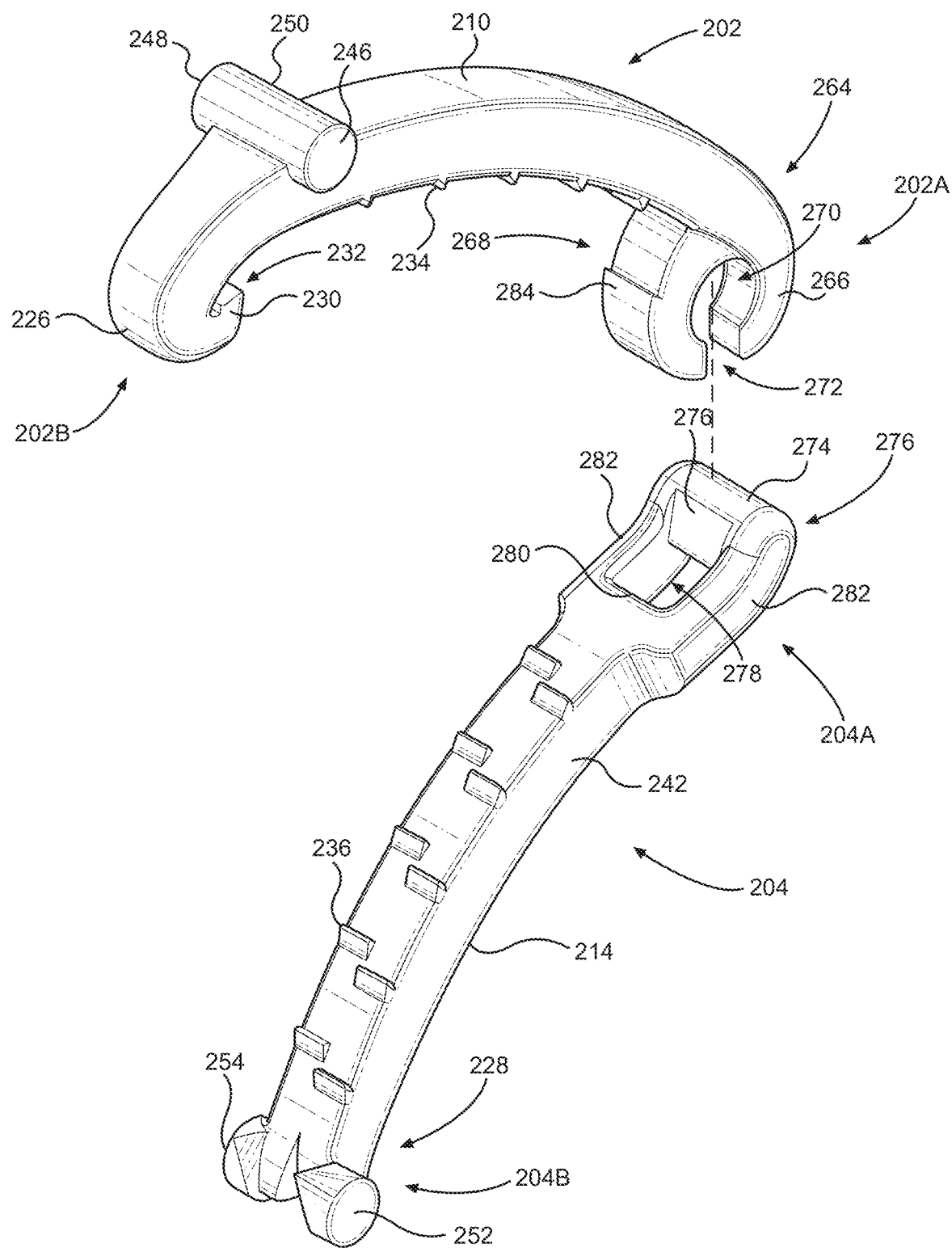
FIG. 6 illustrates an exploded view of the second exemplary embodiment of the surgical clip of FIG. 5.
Figure 7:
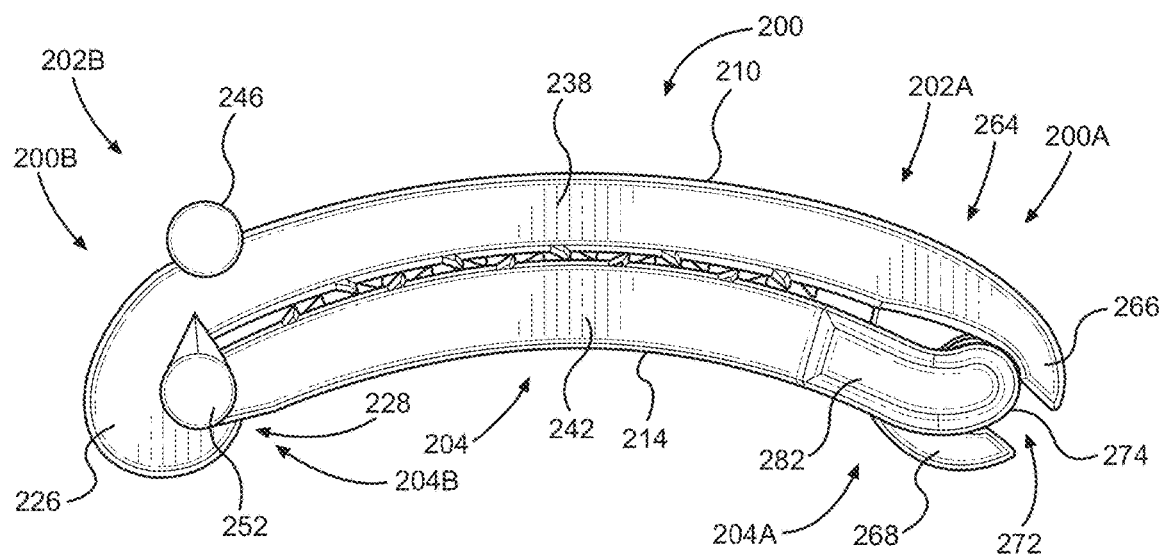
FIG. 7 illustrates a closed configuration of the second exemplary embodiment of the surgical clip of FIGS. 5 and 6.
Figure 8:
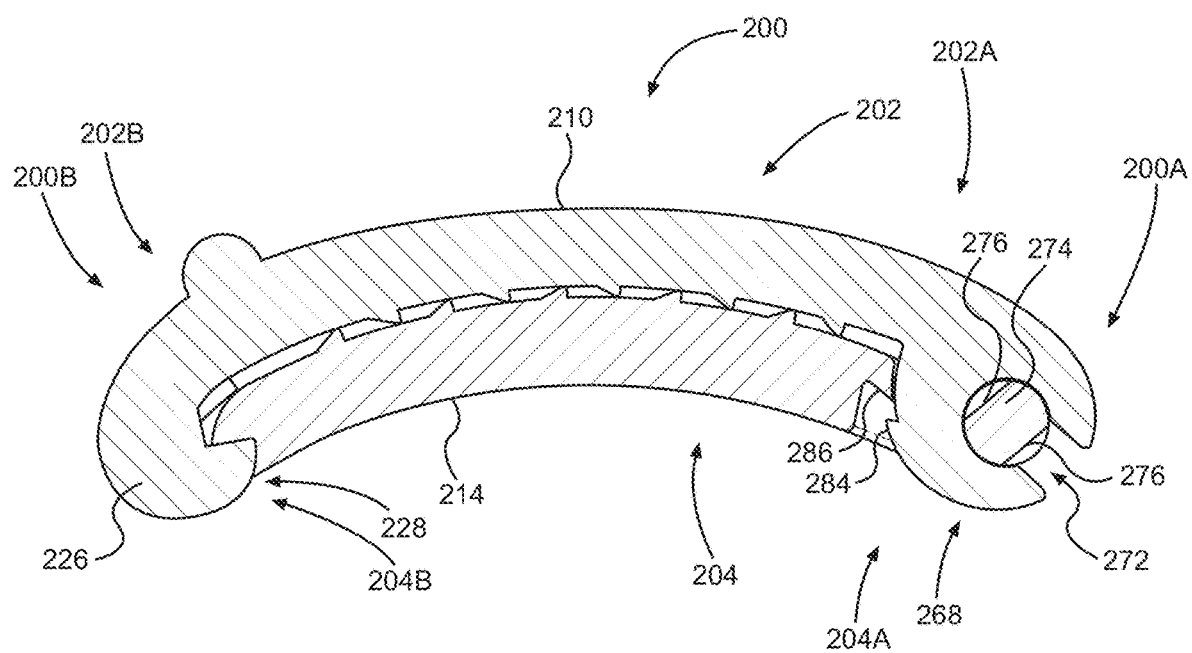
FIG. 8 illustrates a cross-sectional view of the closed configuration of the second exemplary embodiment of the surgical clip of FIGS. 5-7.

The first and second leg members 202, 204 of the surgical clip 200 may be separable. For example, the proximal end portions 202A, 204A of the first and second leg members 202, 204 may be separable at the hinge portion 206. As depicted in FIGS. 5-8, the proximal end portion 202A of the first leg member 202 may include a barrel 264 formed from a proximal elongate member 266 and a distal elongate member 268. The proximal elongate member 266 may form at least a portion of the proximal end portion 202A of the first leg member 202. One or more of the elongate members 266, 268 of the barrel 264 may be arcuate in opposite direction and spaced to form a slot 270 with an opening 272. In some embodiments, the slot 270 may have a recessed concave portion with a substantially circular cross-section. As further depicted in FIGS. 5-8, the slot 270 and the opening 272 may extend the entire width of the first leg member 202, and may be sized to receive a hinge pin 274 on the proximal end portion 204A of the second leg member 204. The hinge pin 274 may include side surfaces 276 on opposite sides of the hinge pin 274. The side surfaces 276 may be substantially flat and allow the surgical clip 200 to be selectively assembled or disassembled when the hinge pin 274 is passed through the opening 272 at a predetermined angle. In other words, the hinge pin 274 may not fit into the opening 272 at any angle other than the predetermined angle. In the example as depicted in FIG. 5, the side surfaces 276 may be disposed at an angle between about 90° and 135° relative to a longitudinal axis of the second leg member 204, such that assembly or disassembly of the surgical clip 200 may be performed when the opening 272 of the second leg member 204 is disposed at the angle relative to the hinge pin 274 of the second leg member 204. Advantageously, the selective assembly/disassembly of the surgical clip 200 may prevent disassembly during the ordinary course of use of the surgical clip 200. For example, the side surfaces 276 may be substantially offset of the opening 272 (e.g., by at least about 90°) when the surgical clip 200 in the closed configuration to prevent the surgical clip 200 from disassembling. It is also contemplated that the surgical clip 200 may be assembled in situ, for example, immediately prior to compression of the surgical clip 200 onto tissue.

As further depicted in FIGS. 5-8, the surgical clip 200 may be assembled by the barrel 264 of the first leg member 202 being received in a channel 278 of the second leg member 204. The channel 278 may be defined by the hinge pin 274, a proximal surface 280 of the second leg member 204, and first and second leg extension members 282 extending between main body of the second leg member 204 and the hinge pin 274. The channel 278 may allow passage of the distal elongate member 268 to transition the surgical clip 200 from the open configuration (e.g., FIG. 5) to the closed configuration (e.g., FIGS. 7-8).

The interaction of the distal elongate member 268 and the channel 278 may provide a second latching or locking mechanism to secure the surgical clip 200 in the closed configuration. For example, the distal elongate member 268 may include a tooth or protrusion 284 that engages an undercut 286 on the proximal surface 280 of the second leg member 204. One or more of the protrusion 284 and the undercut 286 may deflect as the protrusion 284 passes through the channel 278, and the protrusion 284 and the undercut 286 may then provide a latching, interlocking, and/or interference fit to prevent the surgical clip 200 from pivoting to the open configuration (e.g., FIGS. 5-6) from the closed configuration (e.g., FIGS. 7-8). The protrusion 284 may be spaced from the undercut 286 when the surgical clip 200 is in the closed configuration and in the absence of tissue. For example, the first locking mechanism may be engaged in the closed configuration, while the second locking mechanism may not be engaged. The spacing between the protrusion 284 and undercut 286 in the closed configuration may allow flexibility of the surgical clip 200 along its length to accommodate different thicknesses of tissue and to distribute pressure over a width of the tissue as it is ligated. The second locking mechanism may also reinforce the first locking mechanism. For example, the second locking mechanism may prevent the surgical clip 200 from opening when the surgical clip 200 (e.g., the first locking mechanism) wears and/or breaks, such as when uneven absorption and/or degradation of the surgical clip 200 causes the first locking mechanism to disengage. In that sense, the elongated member 268 may include only a single protrusion 284, without any type of ratcheting or tightening mechanism.

The surgical clip 200 may include a first plurality of teeth 234 protruding on the first inner surface 208, and a second plurality of teeth 236 protruding on the second inner surface 212. The teeth 234, 236 may maximize security of compressed tissue and minimize migration. The teeth 234, 236 may be angled toward the proximal end portion 202A of the surgical clip 200 in order to secure the tissue toward the hinge portion 206. The first and second plurality of teeth 234, 236 may include two or more staggered rows of teeth collectively extending the width of the inner surfaces 208, 212. The first plurality of teeth 234 may not engage the second plurality of teeth 236 in the closed configuration to increase the discrete contact points along the length of the surgical clip 200 and enhance security. In some embodiments, one or more of the teeth 234, 236 may be omitted.

The leg members 202, 204 may include one or more bosses along their length to engage a clip applier. For example, the first leg member 202 may include cylindrical bosses 246, 248 protruding perpendicular to each of the opposed side surfaces 238, 240 adjacent to distal end portion 202B of first leg member 202 and immediately inward of hook section 226. In the illustrated example of the surgical clip 200, the bosses 246, 248 may be cylindrical and project outwardly beyond the first outer surface 210 of first leg member 202. The bosses 246, 248 may also be coupled together by a bridge section 250. The second leg member 104 may also include bosses 252, 254 at the distal end portion 204B. The bosses 252, 254 may be cylindrical and protrude perpendicular to each of opposed side surfaces 242, 244 of second leg member 204, extending longitudinally forward beyond the point of tip portion 228. In the practice of ligating tissue, the surgical clip 200 may be designed to be compressed into a latched or locked configuration around the vessel through the use of an appropriate clip applier, such as described in U.S. Pat. No. 5,100,416, the entire disclosure of which is incorporated herein by reference.

Figure 9:
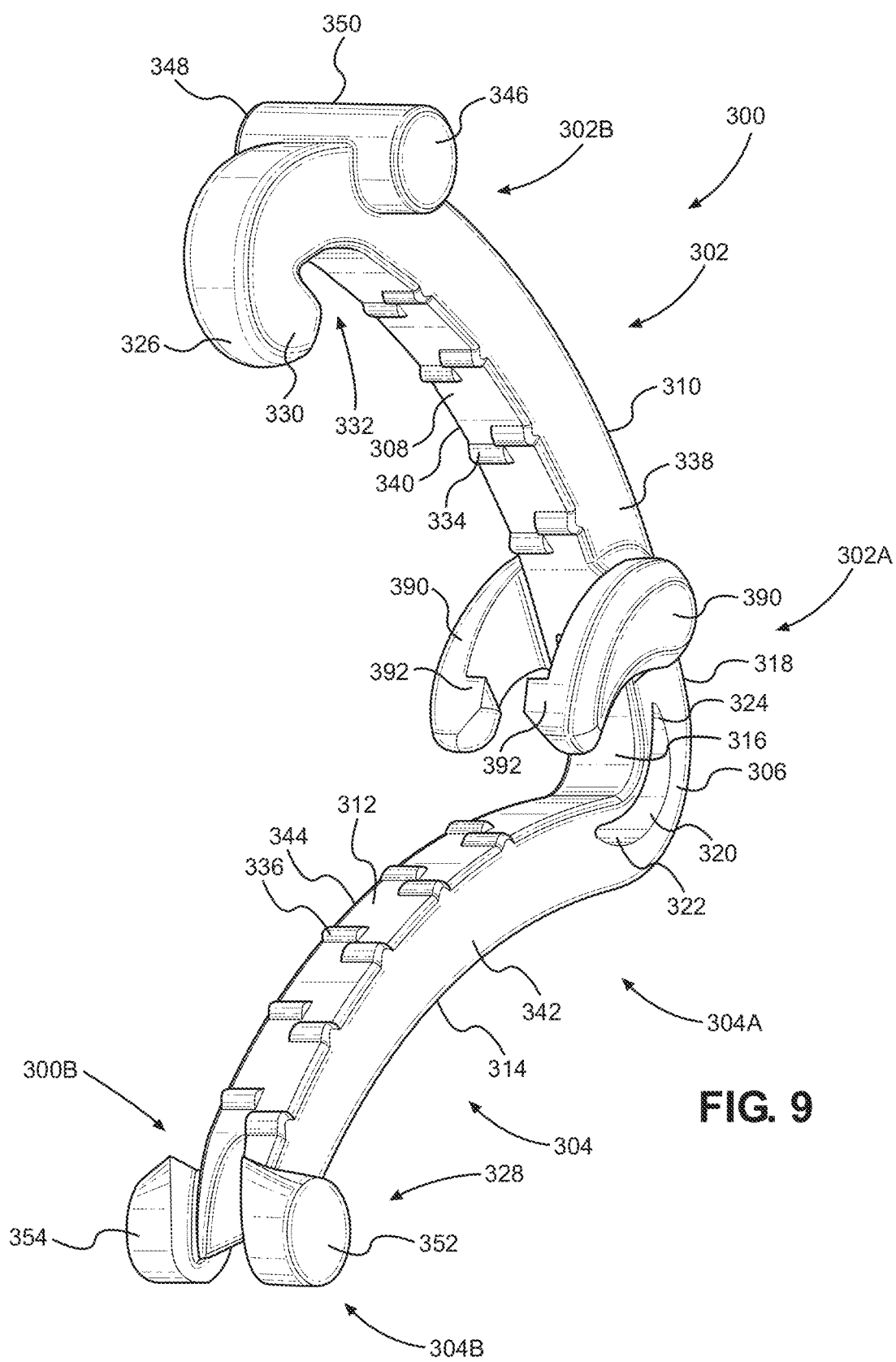
FIG. 9 illustrates a perspective view of a third exemplary embodiment of a surgical clip of the present invention.
Figure 10:
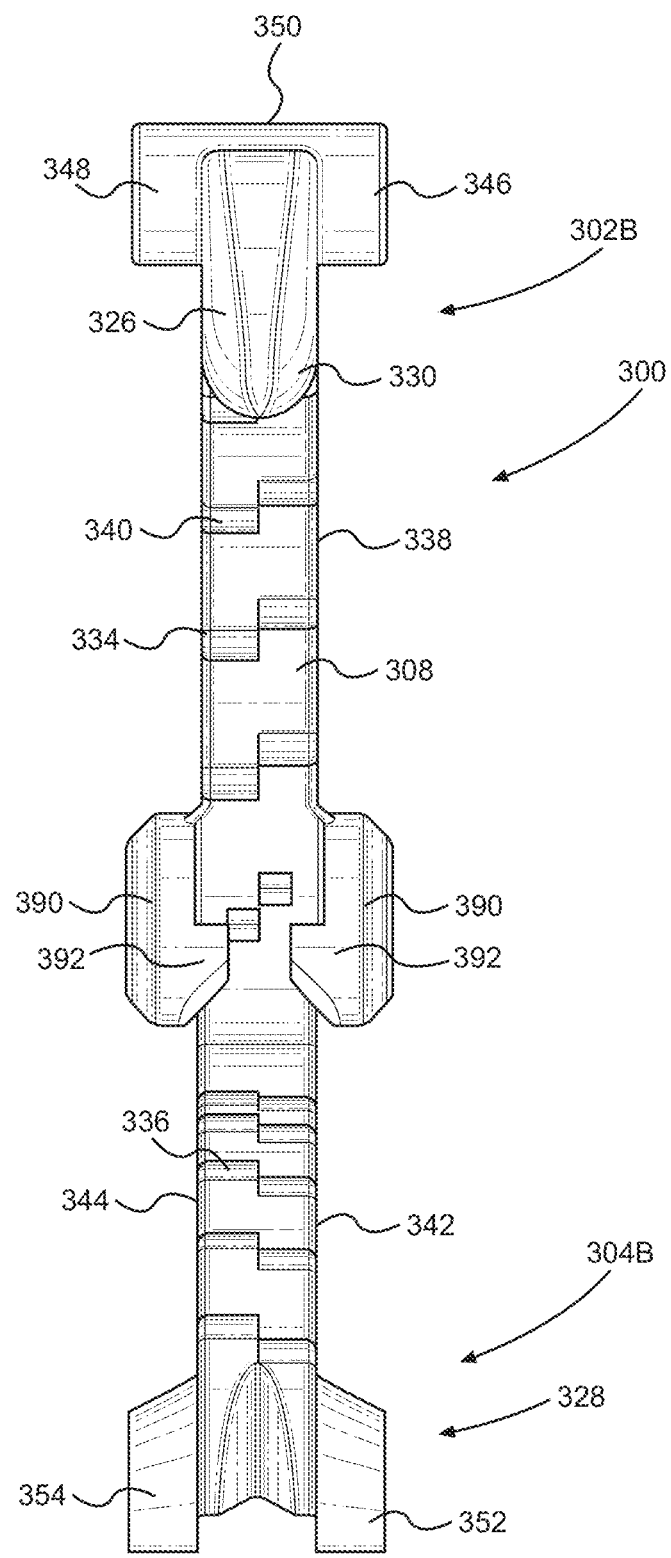
FIG. 10 illustrates a frontal view of the third exemplary embodiment of the surgical clip of FIG. 9.
Figure 11:
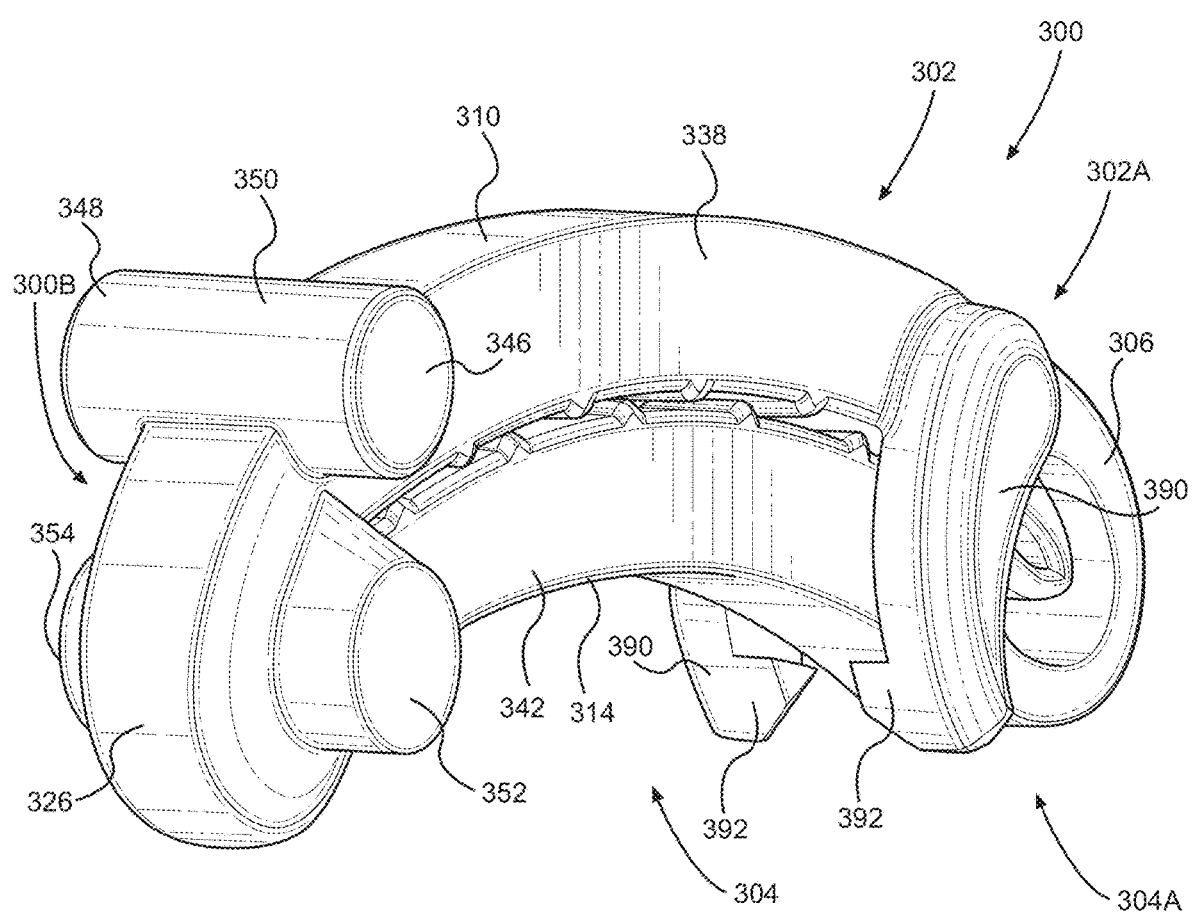
FIG. 11 illustrates a closed configuration of the third exemplary embodiment of the surgical clip of FIGS. 9 and 10.

FIGS. 9-11 illustrate a third exemplary embodiment of a surgical clip 300 of the present invention. The surgical clip 300 may have a proximal end portion 300A and a distal end portion 300B. The surgical clip 300 may further include a first leg member 302 having a proximal end portion 302A and a distal end portion 302B, and a second leg member 304 having a proximal end portion 304A and a distal end portion 304B. The proximal end portions 302A, 304A of the first and second leg members 302, 304 may be connected by a hinge portion 306. The surgical clip 300 may have elements similar to at least one of the surgical clips 100, 200, and may be similarly represented in FIGS. 9-11. For the sake of brevity, the elements and/or aspects of the elements similar to those of the surgical clip 100, 200 may not be discussed with reference to the surgical clip 300.

The first and second leg members 302, 304 may include surfaces having curved portions. For example, the first leg member 302 may include a first inner surface 208 and a first outer surface 310, and the second leg member 304 may include a second inner surface 312 and a second outer surface 314. The first inner surface 308 may have a concave configuration, and the first outer surface 310 may have a convex configuration, or vice versa. The second inner surface 312 may have a convex configuration, and the second outer surface 314 may have a concave configuration, or vice versa. The first and second inner surfaces 308, 312 may be approximated in a closed configuration, and may be resiliently flexible along its length to distribute pressure over a width of the tissue as the tissue is ligated. The first and second inner surfaces 308, 312 may each have a continuous curvature between proximal and distal end portions to provide a favorable compression of tissue.

The hinge portion 306 may have a concave inner surface 316 and a convex outer surface 318. The concave inner surface 316 of hinge portion 306 may continuously join the first inner surface 308 of the first leg member 302 and the second inner surface 312 of the second leg member 304. The convex outer surface 318 of the hinge portion 306 may join the first outer surface 310 of the first leg member 302 and the second outer surface 314 of the second leg member 304. The hinge portion 306 may also include a curved slot 320 located between the curved hinge surfaces 316, 318, and the curved slot 320 may be positioned closer to the concave inner surface 316 than to the convex outer surface 318. The curved slot 320 may extend completely through the hinge portion 306 from side to side and its opposite ends 322, 324 may extend into the proximal end portions 302A, 304A of the first and second leg members 302, 304, respectively. The curved slot 320 may provide added flexibility and resiliency to the hinge portion 306, but the concave inner surface 316 may prevent any portion of a clamped vessel from being trapped within the curved slot 320. In some embodiments, the hinge portion 306 may be resilient and integral to the proximal end portions 302A, 304A of the first and second leg members 302, 304. For example, the hinge portion 306 may bias the surgical clip 300 into an open configuration.

The surgical clip 300 may include one or more latching or locking mechanisms. For example, the first leg member 302 may transition to a hook section 326 at its distal end portion 302B, and the second leg member 304 may transition to a pointed tip portion 328 at its distal end 304B. A distal end portion of the hook section 326 may curve inwardly and point generally toward the concave inner surface 316 of the hinge portion 306. The hook section 326 may have one or more transverse beveled surfaces 330 and a concave inner surface which merges with the first inner surface 308 to define a recess 332. The tip portion 328 may be V-shaped defining a slot configured to receive the beveled surfaces 330, as the hook section 326 deflects around the tip portion 328. The hook section 326 and the tip portion 328 may engage to form a first latching or locking mechanism. For example, the recess 332 may engage with the tip portion 328 in the course of compressing the surgical clip 300 into the closed configuration (e.g., FIG. 11) that may be secured position around a vessel or other tissue.

The surgical clip 300 may also include a second latching or locking mechanism. For example, as depicted in FIGS. 8-11, one or more elongate members 390 may extend from the first leg member 302, from a length between the proximal end portion 302A and the distal end portion 302B. For example, the one or more elongated members 390 may include first and second elongated members 390 extending from opposing sides 338, 340 of the first leg member 302, in an external or "out-board" configuration, and configured to receive the second leg member 304 therebetween. The elongate member(s) 390 may be positioned anywhere on the length of the first leg member 302. In some embodiments, the elongate member(s) 390 may be positioned closer to the proximal end portion 302A than the distal end portion 302B (e.g., on the proximal half of the first leg member 302) in order to secure the proximal end portion 300A of the surgical clip 300. In some embodiments, the elongate member(s) 390 may be positioned closer to the proximal end portion 302A than a centerline of the first leg member 302 (e.g., on the proximal quarter of the first leg member 302) in order to distribute the latching force along the length of the surgical clip 300. The elongate member(s) 390 may extend in an arcuate configuration from the first leg member 302 approximating the arcuate path of the second leg member 304 relative to the first leg member 302. Although FIGS. 8-11 illustrate the elongate member(s) 390 on the first leg member 302, the surgical clip 300 may, additionally or alternatively, include one or more elongated members 390 on the second leg member 304.

As further depicted in FIGS. 8-11, the elongate member(s) 390 may include a tooth or protrusion 392 configured to engage an outer surface 314 of the second leg member 304 to provide the second latching or locking mechanism. The protrusion 392 may be spaced from the outer surface 314 when the surgical clip 300 is in the closed configuration and in the absence of tissue (e.g., FIG. 11). For example, the first locking mechanism may be engaged in the closed configuration, while the second locking mechanism may not be engaged. The spacing between the protrusion 392 and outer surface 314 in the closed configuration may allow flexibility of the surgical clip 300 along its length to accommodate different thicknesses of tissue and to distribute pressure over a width of the tissue as it is ligated. The second locking mechanism may also reinforce the first locking mechanism. For example, the second locking mechanism may prevent the surgical clip 300 from opening when the surgical clip 300 (e.g., the first locking mechanism) wears and/or breaks, such as when uneven absorption and/or degradation of the surgical clip 300 causes the first locking mechanism to disengage. In that sense, each of the elongate member(s) 390 may include only a single protrusion 392, without any type of ratcheting or tightening mechanism.

The surgical clip 300 may include a first plurality of teeth 334 protruding on the first inner surface 308, and a second plurality of teeth 336 protruding on the second inner surface 312. The teeth 334, 336 may maximize security of compressed tissue and minimize migration. The teeth 334, 336 may be angled toward the proximal end portion 302A of the surgical clip 300 in order to secure the tissue toward the hinge portion 306. The first and second plurality of teeth 334, 336 may include two or more staggered rows of teeth collectively extending the width of the inner surfaces 308, 312. The first plurality of teeth 334 may not engage the second plurality of teeth 336 in the closed configuration to increase the discrete contact points along the length of the surgical clip 300 and enhance security. In some embodiments, one or more of the teeth 334, 336 may be omitted.

The leg members 302, 304 may include one or more bosses along their length to engage a clip applier. For example, the first leg member 302 may include cylindrical bosses 346, 348 protruding perpendicular to each of the opposed side surfaces 338, 340 adjacent to distal end portion 302B of first leg member 302 and immediately inward of hook section 326. In the illustrated example of the surgical clip 300, the bosses 346, 348 may be cylindrical and project outwardly beyond the first outer surface 310 of first leg member 302. The bosses 346, 348 may also be coupled together by a bridge section 350. The second leg member 304 may also include bosses 352, 354 at the distal end portion 304B. The bosses 352, 354 may be cylindrical and protrude perpendicular to each of opposed side surfaces 342, 344 of second leg member 304, extending longitudinally forward beyond the point of tip portion 328. In the practice of ligating tissue, the surgical clip 300 may be designed to be compressed into a latched or locked configuration around the vessel through the use of an appropriate clip applier, such as described in U.S. Pat. No. 5,100,416, the entire disclosure of which is incorporated herein by reference.

The surgical clips 100, 200, 300 may be made of any suitable size and may be applied to any number of tissues, such as blood vessels, lymph nodes, nerves, fallopian tubes, or cardiac tissue. The surgical clip 100, 200, 300 may be constructed from any suitable biocompatible material, such as certain metals and polymers. The surgical clip 100, 200, 300 may include absorbable and/or non-absorbable polymeric materials. Exemplary polymeric materials include homopolymers or co-polymers of one or more of polyacetal, polyethylene terephthalate (PET), polybutylene terephthalate (PBT), polyoxymethylene (POM), polymethyl methacrylate (PMMA), polylactic acid (PLA), polyglycolic acid (PGA), and other thermoplastic materials having similar properties that can be injection-molded, extruded or otherwise processed into like articles. However, the surgical clips 100, 200, 300 of the present invention are especially suitable for absorbable material that are weaker and degrade, sometimes at an uneven rate. The surgical clip 100, 300 may be a one-piece integral polymeric body to facilitate manufacturing. It is also contemplated that each of the leg members 202, 204 of the surgical clip 200 may be a one-piece integral polymeric body to facilitate manufacturing.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A surgical clip comprising:
   a first leg member having a first inner surface with a first curvature forming a first vessel clamping surface;
   a second leg member having a second inner surface with a second curvature forming a second vessel clamping surface; and
   an elongate member extending from the first leg member, the elongate member including a tooth;
   wherein the first and second leg members are configured to move between an open configuration where the first and second inner surfaces are spaced apart, and a closed configuration where the first and second inner surfaces are approximated to clamp a vessel or other tissue between the first and second vessel clamping surfaces; and
   wherein the tooth of the elongate member is configured to engage the second leg member to secure the first and second leg members in the closed configuration.

2. The surgical clip of claim 1, wherein the tooth is spaced apart from the second leg member in the closed configuration and in an absence of tissue.

3. The surgical clip of claim 1, wherein a distal end portion of the first leg member includes a hook portion and a distal end portion of the second leg member includes a tip portion, wherein the hook portion is configured to engage the tip portion to secure the first and second leg members in the closed configuration.

4. The surgical clip of claim 1, wherein the elongate member extends from a proximal end portion of the first leg member.

5. The surgical clip of claim 1, further comprising a hinge portion connecting a proximal end portion of the first leg member to a proximal end portion of the second leg member, the hinge portion being configured to pivot the first leg member relative to the second leg member.

6. The surgical clip of claim 5, wherein the hinge portion comprises a slot providing flexibility and resiliency to the hinge portion.

7. The surgical clip of claim 5, wherein the hinge portion is integral to the proximal end portion of the first leg member and the proximal end portion of the second leg member.

8. The surgical clip of claim 5, wherein the hinge portion is configured to bias the first and second leg members to the open configuration.

9. The surgical clip of claim 5, wherein the first leg member is separable from the second leg member at the hinge portion.

10. The surgical clip of claim 5, wherein the proximal end portion of the first leg member comprises a barrel.

11. The surgical clip of claim 10, wherein the barrel includes the elongate member and a slot with an opening sized to receive a hinge pin on the proximal end portion of the second leg member.

12. The surgical clip of claim 1, further comprising at least one boss positioned on a distal end portion of at least one of the first and second leg members.

13. The surgical clip of claim 1, wherein at least one of the first inner surface of the first leg member and the second inner surface of the second leg member comprises a plurality of teeth.

14. The surgical clip of claim 1, wherein the first curvature of the first inner surface of the first leg member is concave, and the second curvature of the second inner surface of the second leg member is convex.

15. The surgical clip of claim 1, wherein the first curvature of the first leg member extends from the respective proximal end portion to the respective distal end portion, and the second curvature of the second leg member extends from the respective proximal end portion to the respective distal end portion.

16. The surgical clip of claim 1, wherein the elongate member extends laterally from a side surface of the first leg member.

17. The surgical clip of claim 1, wherein the surgical clip comprises an absorbable polymer material.

* * * * *